United States Patent [19]
Zoeller et al.

[11] Patent Number: 4,761,497
[45] Date of Patent: Aug. 2, 1988

[54] PROCESS FOR PREPARING 2-NAPHTHANOIC ACIDS AND ESTERS THEREOF

[75] Inventors: Joseph R. Zoeller; Charles E. Sumner, Jr., both of Kingsport, Tenn.

[73] Assignee: Eastman Kodak Company, Rochester, N.Y.

[21] Appl. No.: 107,743

[22] Filed: Oct. 13, 1987

[51] Int. Cl.$^4$ .............................................. C07C 69/76
[52] U.S. Cl. ..................................... 560/100; 562/490; 562/426; 562/462; 562/467; 560/51; 560/56; 560/10
[58] Field of Search ..................... 560/100, 51, 10, 56; 562/490, 426, 462, 467

[56] References Cited

U.S. PATENT DOCUMENTS

| 3,143,567 | 8/1964 | De Pree | 562/490 |
| 3,681,461 | 8/1972 | Kaiser | 562/490 |
| 4,097,674 | 6/1978 | Fried | 562/490 |
| 4,579,968 | 4/1986 | Castaldi | 562/490 |
| 4,582,930 | 4/1986 | Castaldi | 562/490 |
| 4,605,758 | 8/1986 | Schloemer | 562/490 |

FOREIGN PATENT DOCUMENTS 153701  4/1985  European Pat. Off. ............ 562/490

Primary Examiner—Paul J. Killos
Attorney, Agent, or Firm—Charles R. Martin; William P. Heath, Jr.

[57] ABSTRACT

2-Naphtanoic acid or ester thereof is prepared by heating a compound selected from the group consisting of ketals and enol ethers or esters of an alpha-acetyl cinnamic acid or ester thereof at a temperature effective to cyclize the compound and form said 2-naphthanoic acid or ester thereof.

20 Claims, No Drawings

PROCESS FOR PREPARING 2-NAPHTHANOIC ACIDS AND ESTERS THEREOF

BACKGROUND OF THE INVENTION

1. FIELD OF THE INVENTION

The present invention relates to a novel process for preparing 2-naphthanoic acids, particularly substituted acids or esters thereof, by cyclizing a ketal or alpha-enol ether of an alpha-acetyl cinnamic acid or ester thereof.

2. DESCRIPTION OF THE BACKGROUND

Substituted 2-naphthanoic acids and esters thereof are useful as polymer intermediates in the chemical industry. However, the methodology for making these compounds is very sparse. The major problem posed by the synthesis of these compounds is that, for the 2-napthanoic acid derivatives to be useful as polymer intermediates, a second functional group besides the carboxyl group must be present. Moreover, such a functional group must be present as a specific location on the molecule. Thus, a single, specific isomer of a substituted 2-napthanoic acid or ester thereof must be produced out of a large number of distinguishable isomeric naphthanoic acids. The development of such a process is, therefore, of great significant to the industry.

Specific 2-naphthanoic acids have been synthesized by the prior art. For example, see U.S. Pat. Nos. 4,594,445; 4,506,092; and 4,486,605. However, none of these methods are applicable to the general class of 2-naphthanoic acids or esters synthesized by the process of this invention.

Accordingly, there is still a need for a simple and general process for the synthesis of 2-naphthanoic acids and esters thereof having a predictable substitution pattern.

SUMMARY OF THE INVENTION

The invention relates to a process for preparing a 2-naphthanoic acid or ester thereof of the formula

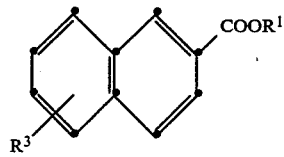

wherein $R^3$ is H, halo or $(C_1-C_{12})$alkoxy, acyloxy, carboxy, carbalkoxy, acyl, alkyl or thioalkyl, and $R^1$ is H, $(C_1-C_{12})$alkyl, $(C_6-C_{20})$aryl, $(C_7-C_{21})$alkylaryl or araalkyl, said process comprising heating a compound selected from the group consisting of a ketal of the formula

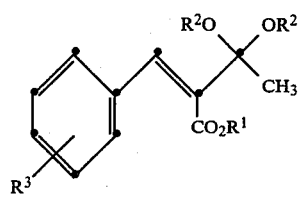

wherein $R^1$ and $R^3$ are as described above, and each $R^2$ is $(C_1-C_{12})$alkyl or the two $R^2$ taken together are $(C_2-C_{12})$alkylene, and an alpha-enol ether of ester of the formula

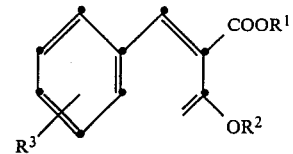

wherein $R^1$ and $R^3$ are as defined above and $R^2$ is $(C_1-C_{12})$alkyl at a temperature effective to cyclize the compound and obtain said 2-naphthanoic acid or ester thereof.

This invention also relates to a process for preparing a 2-naphthanoic acid or an ester thereof which comprises reacting an alpha-acetyl cinnamic acid or ester thereof of the general formula

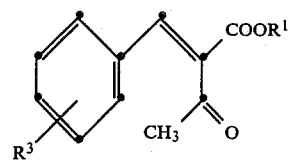

wherein $R^1$ and $R^3$ are as defined above, with a ketalizing agent selected from the group consisting of alkyl glycols and dialkyl acetals, dialkyl ketals, and tri-alkyl orthoesters; said cinnamic acid or ester thereof and said ketalizing agent being present in a proportion and under conditions effective to form a compound selected from the group consisting of a ketal of the formula defined above; and an enol-ether of the formula defined above; heating the thus obtained compound at a temperature effective to cyclize the compound and form said 2-naphthanoic acid or ester thereof.

In addition, this invention also relates to a process for preparing a 2-naphthanoic acid or ester thereof by reacting an acetoacetate ester with a benzaldehyde substituted with H, halo or $(C_1-C_{12})$alkyl, carboxy, carbalkoxy, acyloxy, acyl, alkoxy or alkylthio; said acetoacetate ester and said benzaldehyde being present in a proportion and under conditions effective to produce an alpha-acetyl cinnamic acid or ester thereof of the formula defined above; reacting the alpha-acetyl cinnamic acid or ester thereof with a ketalizing agent selected from the group consisting of alkyl glycols and dialkyl acetals, dialkyl ketals, and tri-alkyl orthoesters said cinnamic acid or ester thereof and said ketalizing agent being present in a proportion and under conditions effective to produce a compound selected from the group consisting of a ketal and an enol-ether of the cinnamic acid or ester thereof of the formulas defined above; and heating the thus obtained compound at a temperature effective to cyclize said compound and form said 2-naphthanoic acid or ester thereof.

A more complete appreciation of the invention and many of the attendant advantages thereof will be readily perceived as the same becomes better understood by reference to the following detailed description of the preferred embodiments thereof.

DESCRIPTION OF THE PREFERRED EMBODIMENTS

The process of the invention for preparing a 2-naphthanoic acid or an ester thereof from a compound such as a ketal or an enol-ether or ester relies on a thermal ring closure of such compound. The cyclization may be performed either in the liquid or vapor phases, with the latter being generally perferred since it can be conducted even in the absence of a solvent and produces generally higher yields of product.

When the cyclization is conducted in the vapor phase, it is done so at a temperature of about 150° to 800° C., and more preferably about 350° to 600° C., and a pressure of about 0.001 mmHg to 3 atm, and preferably about 0.1 mmHg to atmospheric pressure. However, much higher temperatures can also be used without difficulty such as temperatures in excess of about 800° C. These temperatures are easily attainable in an industrial environment.

More commonly, the vapor phase cyclization reaction is conducted at ambient temperature using an inert gas purge to promote the transport of materials across a pyrolysis chamber. However, any feasible pressure below atmospheric pressure may suitably be employed and actually serves to promote the vaporization of the starting acids or esters. By means of example, a pressure of about 10 mmHg can be attained in an industrial environment. Higher pressures than those described above may also be employed, particularly in the case where the starting acids or esters are volatile. However, due to the need to vaporize the starting material the pressure is practically limited to about several atmospheres.

With the vapor phase reaction, the temperature of pyrolysis should be sufficiently high to allow the reaction to proceed at a reasonable rate and attain good conversion rates. The temperature should also be sufficient to completely vaporize the ketal or alpha-enol ether or ester of the alpha-acetyl cinnamic acid or ester thereof. In most cases, this is accomplished by using a reactor temperature of about 470° to 530° C. Except when operating under high vacuum, these temperatures lead to reaction products in which all of the starting alpha-acetyl cinnamic acid ketal, or enol ether or ester, or the ester thereof have been consumed. The best conditions are those that favor rapid vaporization. Thus, the lowest possible pressure should be employed. Industrially, this implies pressures of about 10 mmHg to 60 mmHg since these are generally regarded as the lowest pressures which are economically attainable. However, in the case of more highly valued products, even lower pressures may be used to some advantage. Higher pressures than those described above may also be employed, particularly in the case where the starting ketal or enol ether or ester are volatile. At temperatures below 470° C., the alpha-acetyl cinnamic acid ketal or ester thereof or the related enol ether or ester are about 60% to 70% consumed. Thus, significantly lower temperatures are suitable, particularly if the starting materials are recycled to increase the yield. The lower temperatures are also suitable if contact times with the hot zone in a chamber are lengthened. Since this reaction is usually performed using an inert gas to promote the movement through the tube, this is readily obtainable. A simple reduction at the rate of flow of the gas will increase the contact tie.

When the thermal ring closure is conducted in a liquid phase, an inert solvent is utilized.

Within the context of this invention as inert solvent is defined as a solvent which can withstand the high reaction temperatures involved in the cyclization process without undergoing significant decomposition and which does not react with either the starting material or the product. Any high normal boiling point solvent fitting this criteria may be utilized as the inert solvent at atmospheric pressure. Lower normal boiling point solvents can be used if the reaction is conducted under pressure, i.e., in an autoclave, thereby attaining the desired temperature while preserving the solvent in the liquid phase. When the process is conducted in the liquid phase it is typically done so at a temperature of about 175° to 300° C., and preferably at about 200° to 250° C. The inert solvent must have a normal boiling point equal to or greater than the reaction temperature for the reaction to proceed at atmospheric pressure, or as already indicated if its normal boiling point is lower then the reaction must be conducted at supraatmospheric pressure. Examples of inert solvents are aromatic solvents including heteroaromatic and polycyclic aromatic solvents. alkylated aromatic solvents and halogenated aromatic solvents, saturated cyclic and acyclic hydrocarbons, organic esters including alkyl, phenyl and benzyl esters, and organic ethers including diphenyl ether, among others. More specific examples are methyl and t-butyl esters, decalin, 1-methylnaphthalene, naphthalene and biphenyl. Other suitable inert solvents may also be used including ketones, halogenated aliphatic hydrocarbons aliphatic esters and alcohols, among many others. Solvents which should be avoided since they are not within the above definition of an inert solvent include olefins, primary and secondary amines and carboxylic acids.

Typically, when the cyclization reaction is conducted in the liquid phase, the concentration of the alpha-enol ether or ester or the ketal of the alpha-acetyl cinnamic acid or the ester thereof in the solvent may be varied over a broad range. Typically, the ketal or alpha-enol ether or ester is present in an amount of about 0.01 moles to 1 moles per liter of the solvent.

Suitable $R^1$ groups in the structures of the compounds illustrated and discussed above include H; alkyl groups such as methyl, ethyl, propyl, butyl, pentyl, hexyl, decyl, and the like; aryl groups such as phenyl, naphthyl, and the like; alkyaryl such as tolyl, anthryl, and the like; arslkyl such as benzyl, phenylethyl, phenylpropyl, phenylbutyl, and the like.

Illustrative of suitable $R^2$ groups in the structures are methyl, ethyl, propyl, butyl, pentyl, hexyl, decyl, and the like, and examples of suitable $R^2$ groups in the ketal (I) when taken together are ethylene, trimethylene, tetramethylene, and the like.

Exemplary of $R^3$ groups are hydrogen, halo such as chloro, bromo and fluoro; carboxy; alkyl such as described for $R^1$ and $R^2$; alkoxy such as methoxy, ethyoxy, propoxy, butoxy, pentoxy, and the like; acyl such as ethanoly, propanoyl, butanoyl, pentanoyl and the like; acyloxy such as ethanoyloxy, propanoyloxy, butanoyloxy, pentanoyloxy, and the like; carbalkoxy such as methoxycarbonyl, ethyoxycarbonyl, propoxycarbonyl, butoxycarbonyl, etc.; alkylthio such as methylthio, ethylthio, propylthio, butylthio, pentylthio, etc.

Also, the aromatic ring of the alpha-vinyl cinnamic acid or ester thereof may be substituted at any position, although preferred positions are the ortho and para positions of the ring with respect to the carboxy-containing residue. If the ring substitution is in either the para or ortho position, the products are entirely predictable. More specifically, para-substituted ketals or enol-ethers of alpha-acetyl cinnamic acids or esters thereof undergo ring closure to yield 6-substituted 2-naphthanoates and ortho-substituted alpha-acetyl cinnamates yield 8-substituted 2-naphthanoates. On the other hand, the meta-substitution of the aromatic ring of the cinnamic acid or ester thereof leads to a mixtures of the isomeric 5- and 7-methoxy substituted 2-naphthanoates, e.g., with the latter predominating slightly in the case of the methyl m-methoxy alpha-acetyl cinnamate ketal or enol ether. Clearly, the present invention enables the preparation of these unique compounds, although they are not obtainable in a form which is substantially free of other isomers.

Although the $R^1$ substituent of the cinnamic acid ester may be derived form an alkyl or aryl group, the methyl ester is preferred due to its high volatility, particularly when the cyclization step is conducted in the vapor phase. The selection of the specific ester derivative is of lesser importance when the reaction is conducted in the liquid phase, and therefore there is more latitude in the choice of the specific ester utilized.

Enol ethers of alpha-acetyl cinnamic acids or the esters thereof can be obtained by heating the related ketals at a temperature of about 25° to 300° C., preferably 75° to 250° C. and more preferably above 125° C. or by distilling the ketal. Enol ethers of alpha-acetyl cinnamic acids or esters thereof can also be prepared by other methods known in the art.

In one particular embodiment of the invention, the heating step producing the cyclization of the ketal of a substituted alpha-acetyl cinnamic acid or ester thereof is heated at the above temperatures to produce the related alpha-enol ether of the alpha-acetyl cinnamic acid or ester thereof, and then the thus obtained alpha-enol ether of the alpha-acetyl acid cinnamic or ester thereof is heated at a temperature effective to cyclize said enol ether to form the substituted 2-naphthanoic acid or ester thereof. When the cyclization of the alpha-enol ether of the alpha-acetyl cinnamic ester thereof is conducted in the vapor phase, it is preferably done at a temperature of about 150° to 800° C., and more preferably about 350° to 600° C., and a pressure of about 0.001 mmHg to 3 atm, and more preferably about 0.1 mmHg to atmospheric pressure. However, much higher temperatures can also be used without difficulty, such as temperatures in excess of about 800° C. More commonly, the conditions under which the cyclization of the alpha-enol ether cinnamic acid or ester thereof is conducted are similar to the conditions described above for the cyclization of the related ketal. It should be noted that the conversion of the ketal to the cyclic product proceeded through the formation of an alpha-enolic structure.

When the thermal ring closure of the alpha-enol ether cinnamic acid or ester thereof is conducted in a liquid phase, an inert solvent is utilized. Typically, solvents as those described above for the similar reaction of the related ketal are useful in this case. When the process is conducted in a liquid phase, it is preferably done at a temperature of about 175° to 300° C., and more preferably about 200° to 250° C. Similar conditions are also suitable for the cyclization of the alpha-enol ester of cinnamic acid or ester thereof. Up to the present time the prior art has not addressed in general, or by means of examples, the ring closure of ketals of alpha-acetyl cinnamates to generate 2-naphthanoates. Furthermore, not even instances of simpler benzalacetone ketals being used to generate a naphthalane are known.

In another aspect of the invention, the 2-naphthanoic acids or esters thereof are prepared from an alpha-acetyl cinnamic acid or ester thereof of the formula defined above and a ketalizing agent, and the thus obtained ketal is then cyclized by heating.

A number of methods for the ketalization of ketones are known (Gasparrini, F., Giovannoli, M., and Misiti, D., Tetrahedron 40:1491 (1984) and references cited therein). However, no known applications of these methods to alpha-acetyl cinnamic acid or esters thereof are known.

The ketal of the substituted alpha-acetyl cinnamic acid or ester thereof may be obtained by reacting an alpha-acetyl cinnamic acid or ester thereof with a ketalizing agent. Suitable ketalizing agents are alkyl glycols and dialkyl acetals, dialkyl ketals, and tri-alkyl orthoesters such as ($C_2$-$C_{12}$)glycols, e.g., 1,2- or 1,3-glycols, ($C_1$-$C_{12}$)alkyl orthoesters and ($C_1$-$C_{12}$)dialkyl-ketals or acetals derived from ($C_1$-$C_{12}$)ketones or aldehydes, respectively. Examples of suitable glycols and orthoformates are neopentyl glycol, propanediol, 1,2- and 1,3-ethylene glycol, trimethyl orthoformate and the like. Preferred are alkyl glycols and alkyl orthoformates having 1 to 5 carbon atoms. Alkyl glycols and di- and tri-alkyl orthoformates are commercially available or may be prepared by methods known in the art which need not be described herein.

The reaction of an alpha-acetyl cinnamic acid or ester thereof with a ketalizing agent is preferably conducted at a temperature of about 25° to 250° C., and more preferably about 40° to 200° C. Typically, this reaction is conducted at atmospheric pressure. However, other pressures are also suitable.

In a still more preferred embodiment of the invention, the reaction of the alpha-acetyl cinnamic acid or ester thereof with the ketalizing agent is conducted in the presence of a transition metal catalyst and an acid catalyst. Preferred are strong acids such as sulfuric acid, trifluoroacetic acid, hydrochloric acid or sulfonic acid or an acidic resin such as as acid-exchange resin. Acidic resins are commercially available or can be prepared by methods known in the art which need not be described herein. A preferred acid resin is Amberlyst-15 ®. The transition metal catalyst for the ketalization reaction of the invention can be any transition metal olefin isomerization catalyst which isomerizes the unreacted isomer of the ketone reactant into a more reactive isomer and thereby provides a constant supply of reactive ketone. Preferred isomerization catalysts are Group VIII metal catalysts, e.g., rhodium, ruthenium, cobalt and palladium catalysts and derivatives thereof such as cobalt hydrides, and palladium hydrides, among others. Particularly preferred among the transition metal catalysts are carbonylhydride tris(triphenylphosphine)rhodium and hydridochlorocarbonyl tris(triphenylphosphine) ruthenium. The transition metal catalyst will always be used in catalytic amounts which usually fall in the range of 0.01 to 0.001 mole/mole of α-acetyl cinnamate acid or ester. The proportion of the acid catalyst to transition metal catalyst generally ranges from about 10:1 to 10,000:1, and more preferably 50:1 to 5,000:1 by weight.

In the reaction of the substituted alpha-acetyl cinnamic acid or ester thereof to ketalizing agent may vary widely but ordinarily fall in the range of about 1:1 to 1:5 molar equivalents, preferably about 1:1 to 1:3 molar equivalents. The reaction temperatures employed are those sufficient to effect the ketalization reaction and normally fall in the range of about 25° to 250° C., preferably about 40° to 200° C. The reaction proceeds readily at atmospheric pressure but the reaction can be conducted under pressure if desired.

The ketalization reaction is generally conducted in a liquid phase and an inert solvent may be added. Within the context of this invention, an inert solvent is defined as a solvent which can withstand the reaction temperatures involved in the ketalization reaction without undergoing significant decomposition and without detracting from the formation of the product. Examples of inert solvents are acyclic, cyclic and aromatic hydrocarbons, halides thereof or their azeotropes formed with water, alcohols and glycols from which the alkylene and alkyl residues of the $R^2$ substituents of the ketals are derived. A preferred group of solvents are alcohols or glycols such as methanol, ethanol, and ethylene glycol.

Alpha-acetyl cinnamic acid or ester thereof may be obtained by reacting a compound such as acetoacetic acid or an ester thereof of the formula $CH_3$—CO—$CH_2COOR^1$ wherein $R^1$ is an defined above or acetylacetone with a benzaldehyde substituted with $R^3$, wherein $R^3$ is as defined above. The Knoevenagel condensation of aromatic aldehydes and acetoacetic esters is a well known and efficient process for generating alpha-acetyl cinnamic acid esters (Jones, Org. Reactions 15:204 (1967), the content of which is incorporated herein by reference). The reaction of acetoacetone with a substituted aromatic benzaldehyde can also be conducted under conditions similar to those of the Knoevenagel reaction.

In general, the reaction of acetoacetic acid or an ester thereof or the acetylacetone with the benzaldehyde is conducted at a temperature of about 0° to 250° C., and more preferably about 50° to 150° C., and at a pressure of about 0.1 mmHg to 10 atm, preferably 1 atm. In this reaction, the acetoacetic acid or ester thereof or the acetylacetone and the benzaldehyde are preferably present in a proportion of about 25:1 to 1:25, and more preferably about 1:1 to 1:2 by weight.

In an alternative embodiment of the invention where the transition metal catalyst is not included, the process of the invention may be conducted by utilizing a trailkyl orthoformate and an alpha-acetyl cinnamic acid or ester thereof in the presence of a solvent and an acidic resin raising the temperature beyond the temperatures specified above. The reaction can be conducted while maintaining a continuous nert gas purge to remove the by-product alkyl ester as it is formed. This procedure yields the ketal after several hours. This embodiment is available for the formation of di-alkyl ketals, the thus formed ketals are obtained with a high yield, in excess of 80 weight percent.

Cyclic ketals such as those generated by ketalizing with vicinal glycols are also useful in this process. Those ketals are generally generated in the prior art by treating a ketone with an excess of the glycol in the presence of an acidic catalyst while water produced by the reaction is continuously removed. However, this prior art method is not applicable to the synthesis of the present ketals of alpha-acetyl cinnamic acids or esters thereof. In the case of the cyclic ketals, there is no alternative to including a transition metal catalyst as described above if high yields and conversions are desired. In the case of the cyclic ketals raising the temperatures will not make the reaction proceed.

The cyclization of the ketals or alpha-enol ethers or esters of the invention to obtain 2-naphthanoic acids or esters thereof proceeds with a crude yield of at least about 70 weight percent to 85 weight percent and the product is obtained with a purity generally in the range of 80 weight percent to 90 weight percent.

The substituted 2-naphthanoic acid may be purified by any of a number of standard methods, including chromatography, distillation or crystallization, among others. After purification, the yield of the substituted 2-naphthanoic acid based on the amount of starting alpha-acetyl cinnamic acid or ester thereof is greater than about 24 mole percent to 65 mole percent, depending on the nature of the substituent on the aromatic ring of the starting alpha-acetyl cinnamic acid or ester thereof.

Having now generally described this invention, the same will be better understood by reference to certain specific examples, which are included herein for purposes of illustration only and are not intended to be limiting of the invention or any embodiment thereof, unless so specified.

EXAMPLES

In all the examples listed below the intermediate ketals are identified on the basis of their proton NMR, infrared (IR), and mass spectra including an exact mass for the molecular ion. The final 2-naphthanoic products are identified on the basis of their proton NMR, IR, and mass spectra.

EXAMPLE 1

Ketalization-Cyclization With Acidic Resin and Catalyst

A solution is prepared in a 50-mL flask containing 10.20 grams (0.050 moles) of methyl alpha-acetyl cinnamate and 10 milligrams (11 micromoles) of hydridocarbonyl (tris-triphenyl-phosphine)rhodium in 30 mL of 1/1 trimethyl orthoformate/methanol. To this solution are added 1 to 1.2 grams of an acid resin, e.g., Amberlyst-15, and the mixture is stirred at room temperature for 5 to 16 hours. The reaction is 98% complete in 5 to 7 hours. Longer reaction times are generally allowed more out of convenience than necessity.

The reaction mixture is then filtered to remove the resin, swirled with 1 gram of a slightly basic resin, e.g., Amberlyst-21, filtered again, washed with 1/1 trimethyl orthoformate/methanol, and the solvent removed in vacuo. A sample is examined spectroscopically (NMR, IR, mass spectra) to confirm the identity of the ketal. The crude product is a ketal weighing 12.84 grams. A small amount of enol ether is also present, whose identity is also confirmed by mass spectroscopy.

The crude ketal (8.76 grams, 0.035 moles if the ketal is pure) is pyrolyzed using a simple drip-type pyrolysis unit which consisted of a 1 inch diameter quartz tube, filled with 20 cm of fine chips, e.g., Vycor ® chips, and placed in a 12 inch electric furnace. A thermal couple is used to monitor temperature and a furnace is used to maintain the temperature between 475° to 495° C. The movement of the material through the tube is promoted by an inert gas purge (50 mL/hour) and the crude, liquid ketal is added at a rate of 2 mL/hour. This procedure results in 5.78 grams of crude methyl 2-naphthanoate which is purified chromatographically to give 3.80 grams (0.0204 moles) of pure methyl 2-napthanoate. This represents a yield of 60% from the starting methyl alpha-acetyl cinnamate.

EXAMPLE 2

Ketalization-Cyclization Without Catalyst

This exemplifies a ketalization-cyclization in which the ketal is generated in the absence of a transition metal catalyst.

A solution of methyl p-bromo alpha-acetyl cinnamate (mixture of olefin isomers, 14.15 grams, 0.050 moles), 15 mL trimethyl orthoformate and 15 mL of methanol is prepared in a 50-mL, round-bottom flask equipped with a thermometer inlet, a gas inlet consisting of a pipette connected to a nitrogen source and supported in a thermometer adaptor and a gas outlet. To this solution are added 1.2 grams of an acidic resin, e.g., Amberlyst-15, and a slow, consistent inert gas purge is established through the solution. The solution is stirred magnetically and maintained at a temperature of 55° C. for a period of 5.5 hours. The material is then filtered, neutralized by swirling the mixture with a slightly basic resin, e.g., Amberlyst-21, and the solvent is removed in vacuo. The crude ketal, whose identity is verified spectroscopically, weights 16.42 grams.

A sample of the crude ketal (13.30 grams) is pyrolyzed as described in Example 1 to give 4.80 grams of methyl 6-bromo-2-naphthanoate after recrystallization from methanol. This represents an overall yield of 45% from the starting methyl p-bromo-alpha-acetyl cinnamate.

EXAMPLE 3

Following the procedure in Example 1, methyl 6-isopropyl 2-naphthanoate is obtained with a 63% overall yield from methyl p-isopropyl-alpha-acetyl cinnamate.

EXAMPLE 4

Following the procedure in Example 1, with the exception that the final product is isolated by crystallization from methanol, methyl 6-methyl 2-naphthanoate is obtained with a 53% yield from methyl p-methyl alpha-acetyl cinnamate.

EXAMPLE 5

Following the procedure in Example 2, with the exception that the intermediate ketal is isolated by crystallization with an 85% yield, methyl p-carbomethoxy alpha-acetyl cinnamate is converted to 2,6-maphthalene dicarboxylic acid dimethyl ester with an overall yield of 42%. (Yield soley for pyrolysis=49%)

EXAMPLE 6

Following the procedure in Example 1, methyl p-methoxy alpha-acetyl cinnamate is converted to methyl 6-methoxy 2-naphthanoate with a yield of 27%.

EXAMPLE 7

Following the procedure in Example 1, methyl o-methoxy alpha-acetyl cinnamate is converted with a 34% yield to methyl 8-methoxy-2-naphthanoate.

EXAMPLE 8

Following the procedure in Example 1, methyl m-methoxy alpha-acetyl cinnamate is converted to a mixture of 5- and 7-methoxy substituted 2-naphthanoic acid methyl esters which are obtained in yields of 19% and 24%, respectively.

EXAMPLE 9

Enolization-Cyclization Without catalyst

This example demonstrates the utility of the enol ethers in the cyclization.

A crude dimethyl ketal of methyl p-methyl alpha-acetyl cinnamate is generated as in Example 2 and then instead of pyrolyzing the material directly, it is distilled at 0.5 to 1.5 mmHg (bp: 125° to 130° C.). The NMR spectrum of the product indicates that the compound is a 1:1 mixture of the olefinic isomers of the methyl enol ether of methyl p-methyl alpha-acetyl cinnamate contaminated with about 10% of the related ketal. The enol ether is pyrolyzed as in Example 1 to give a 69% yield of methyl 6-methyl 2-naphthanoate as calculated from the enol ether.

EXAMPLE 10

This example demonstrates the feasibility of operating the reaction in the liquid phase. A 1.02 gram (3.86 mmol) sample of crude methyl p-methyl alpha-acetyl cinnamate dimethyl ketal, is generated as described in Example 2, dissolved in 51 mL of 1-methyl naphthalene and heated at reflux for 6 hours. The reaction mixture is added to a chromatography column and eluted first with hexane until no more 1-methylnaphthalene is detectable in the hexane fractions. The product is then obtained by further eluting the material with 5% ethyl acetate in hexane to give 0.330 grams (1.65 mmol, 43%) of pure methyl 6-methyl 2-naphthanoate.

EXAMPLE 11

Cyclic Ketalization-Cyclization

This example demonstrates the feasibility of using cyclic ketals in this process.

The ethylene glycol ketal of methyl p-methyl alpha-acetyl cinnamate is prepared as follows. To a 500-mL, three-neck flask equipped with a Dean-Stark trap are added methyl alpha-acetyl-4-methylcinnamate (51 grams; 0.234 mol), ethylene glycol (50 grams; 0.806 mol), carbonylhydrido tris(triphenylphosphine) rhodium (0.250 gram; 0.27 mol), an acidic resin, e.g., Amberlyst-15 (1.00 gram) and cyclohexane (150 mL). The mixture is heated at reflux for 5.5 hours while the water of reaction is collected. When 20 mL of the ethylene glycol/water layer are collected in the Dean-Stark trap, it is removed from the trap and an additional 20 mL of dry ethylene glycol is added to the reaction mixture. The mixture is sampled periodically and analyzed by GC and H NMR. The initial ratio of the Z isomer to the E isomer is 1.3:1.0. This ratio remained essentially constant throughout the reaction. After 5 hours the ketone is about 90% converted to the ethylene ketal. Of the unconverted ketone, the ratio of Z to E isomers as determined from the H NMR spectrum is still about 1.3:1.

A sample of this ketal (3.10 grams, 11.8 mmol) is pyrolyzed as described in Example 1 to generate 2.09 grams of crude methyl 6-methyl alpha-acetyl cinnamate which is about 77% pure by gas chromataographic assay.

EXAMPLE 12

Reduced Pressure

This example demonstrates the feasibility of running this process under reduced pressures.

A toluene solution of 40.0 grams of the dimethyl ketal of methyl p-carbomethoxy alpha-acetyl cinnamate is generated as in Example 5, pyrolyzed using a flash pyrolysis unit whose flash evaporation section consisted of a 300-mL, three-necked, round-bottom flask which is filled about 33% full with coarse chips, e.g., Vycor ® chips and fitted with a thermocouple well in one neck, an addition funnel containing the solution in the second neck and an outlet to the pyrolysis unit in the third neck. The pyrolysis unit is identical to the unit described in Example 1 except that the outlet end of the unit is now connected to a vacuum line. The temperature in the pyrolysis unit is maintained at 490° C. and the vacuum set initially at 0.5 mmHg.

The flash unit is heated to 300° C. and the addition of the ketal solution is initiated. The rate of addition of the ketal solution is slow enough to maintain the temperature in the flash unit and to allow the pressure to return to nearly the desired level between drops. This takes nearly an hour. The resultant product weighs 30.0 grams and its assay by gas chromatography indicates that the product contains 5.1 grams of the desired 2,6-naphthalene dicarboxylic acid dimethyl ester. The remaining materials consist of the corresponding enol ethers and the intermediate dihydronaphthalene which are the expected intermediates in the conversion. This finding is supported by gas chromatography-mass spectral analysis. Considering these intermediates as starting material equivalents, this represents a yield of 53% and a conversion of 31%.

The invention now being fully described, it will be apparent to one of ordinary skill in the art that many changes and modifications can be made thereto without departing from the spirit or scope of the invention as set forth herein.

What is claimed is:

1. A process for preparing a 2-naphthanoic acid or ester thereof of the formula

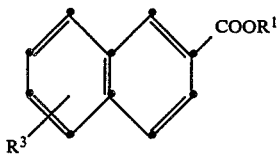

wherein $R^3$ is H, halo or $(C_1-C_{12})$ alkoxy, acyloxy, carboxy, carbalkoxy, acyl, alkyl or thioalkyl, and $R^1$ is H, $(C_1-C_{12})$alkyl, $(C_6-C_{20})$aryl, $(C_7-C_{21})$alkaryl or araalkyl, said process comprising heating a compound selected from the group consisting of a ketal of the formula

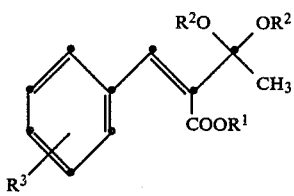

wherein $R^1$ and $R^3$ are as described above, and each $R^2$ is $(C_1-C_{12})$alkyl or the two $R^2$ taken together are $(C_2-C_{12})$alkylene, and an alpha-enol ether of ester of the formula

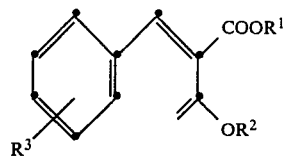

wherein $R^1$ and $R^3$ are as defined above and $R^2$ is $(C_1-C_{12})$alkyl or $(C_2-C_{12})$ acyl at a temperature effective to cyclize the compound and obtain said 2-naphthanoic acid or ester thereof.

2. The process of claim 1, wherein the heating is conducted in the vapor phase at a temperature of about 150° to 800° C. and a pressure of about 0.001 mmHg to 3 atm.

3. The process of claim 2, wherein the temperature is about 350° to 600° C., and the pressure is about 0.1 mmHg to atmospheric pressure.

4. The process of claim 1, wherein the heating is conducted in the presence of a solvent at a temperature of about 175° to 300° C.

5. The process of claim 4, wherein the solvent has a normal boiling point which is higher than or the same as the reaction temperature.

6. The process of claim 4, wherein the solvent has a normal boiling point which is lower than the reaction temperature; and the reaction is conducted under a pressure higher than about atmospheric pressure.

7. The process of claim 1, further comprising distilling the ketal prior to said heating step.

8. The process of claim 1, wherein the heating step is conducted by heating the ketal at a temperature of about 75° to 300° C. to obtain an alpha-enol ether of the cinnamic acid or ester thereof; and then heating the alpha-enol ether of the cinnamic acid or ester thereof at a temperature effective to cyclize said alpha-enol ether and obtain said 2-naphthanoic acid or ester thereof.

9. The process of claim 8, wherein the heating of the alpha-enol ether cinnamic acid or ester thereof is conducted in the vapor phase at a temperature of about 150° to 800° C.

10. The process of claim 9, wherein the temperature is about 350° to 600° C.

11. The process of claim 3, wherein the heating of the alpha-enol ether of the cinnamic acid or ester thereof is conducted in an inert solvent at a temperature of about 175° to 300° C.

12. The process of claim 11, wherein the solvent has a normal boiling point which is higher than or the same as the reaction temperature.

13. The process of claim 11, wherein the solvent has a normal boiling point which is lower than about the reaction temperature; and the reaction is conducted under a pressure greater than about atmospheric pressure.

14. The process of claim 1, wherein the $R^3$ substituent of the ketal is at the ortho or para position.

15. A process for preparing a 2-naphthanoic acid or an ester thereof of the formula

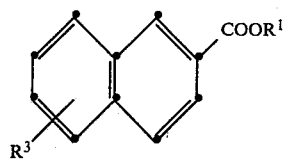

wherein $R^3$ is H, halo or $(C_1-C_{12})$alkoxy, acyloxy, carboxy, carbalkoxy, acyl, alkyl or thioalkyl, and $R^1$ is H, $(C_1-C_{12})$alkyl, $(C_6-C_{20})$aryl, $(C_7-C_{21})$alkaryl or araalkyl, said process comprising reacting an alpha-acetyl cinnamic acid or ester thereof of the formula

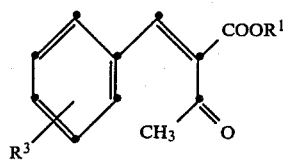

wherein $R^1$ and $R^3$ are as defined above, with a ketalizing agent selected from the group consisting of alkyl glycols and di- and tri-alkyl orthoesters; said cinnamic acid or ester thereof and said ketalizing agent being present in a proportion and under conditions effective to form a compound selected from the group consisting of a ketal of a cinnamic acid or ester thereof of the formula

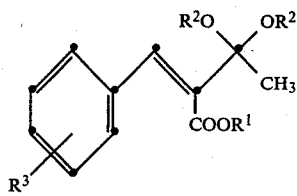

wherein $R^1$ and $R^3$ are as defined above, and $R^2$ is $(C_1-C_{12})$alkyl or the two $R^2$ taken together are $(C_1-C_{12})$akylene, or an alpha-enol ether of a cinnamic acid or ester thereof of the formula

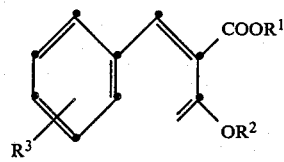

wherein $R^2$ is $(C_1-C_{12})$alkyl $(C_2-C_{12})$ acyl and heating said compound at a temperature effective to cyclize said compound and form said 2-naphthanoic acid or ester thereof.

16. The process of claim 15, wherein the reaction of the alpha-acetyl cinnamic acid or ester thereof with the ketalizing agent is conducted at a temperature of about 25° to 250° C.

17. The process of claim 15, wherein the reaction of the alpha-acetyl cinnamic acid or ester thereof with the ketalizing agent is conducted in the presence of a transition metal catalyst and an acid catalyst, and the proportion of said acid to said catalyst is about 10:1 to 10,000:1.

18. The process of claim 17, wherein the acid is an acidic resin.

19. The process of claim 17, wherein the catalyst is selected from the group consisting of rhodium, palladium, cobalt and ruthenium catalyst.

20. A process for producing a 2-naphthanoic acid of the formula

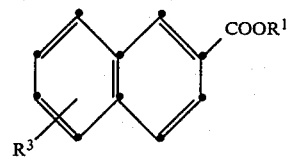

wherein $R^3$ is H, halo or $(C_1-C_{12})$alkoxy, acyloxy, carboxy, carbalkoxy, acyl, alkyl or thioalkyl, and $R^1$ is H, $(C_1-C_{12})$alkyl, $(C_6-C_{20})$aryl, $(C_7-C_{21})$alkaryl or araalkyl, said process comprising reacting an acetoacetate ester with a benzaldehyde substituted with H, halo or, $(C_1-C_{12})$alkyl, carboxy, carbalkoxy, acyloxy, acyl, alkoxy or alkylthio; said acetoacetate ester or acetylacetone and said benzaldehyde being present in a proportion and under conditions effective to form an alpha-acetyl cinnamic acid or ester thereof of the formula

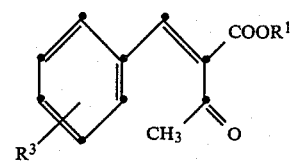

wherein $R^1$ and $R^3$ are as defined above; reacting said alpha-acetyl cinnamic acid or ester thereof with a ketalizing agent selected from the group consisting of alkyl glycols and di- and tri-alkyl orthoesters; said cinnamic acid or ester thereof and said ketalizing agent being present in a proportion and under conditions effective to form a compound selected from the group consisting of a ketal of a cinnamic acid or ester thereof of the formula

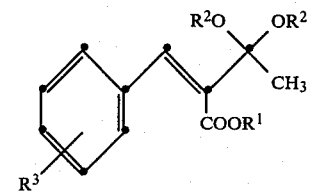

wherein $R^1$ and $R^3$ are as defined above, and $R^2$ is $(C_1-C_{12})$alkyl or the two $R^2$ taken together are $(C_1-C_{12})$alkylene, and an alpha-enol ether of a cinnamic acid or ester thereof of the formula

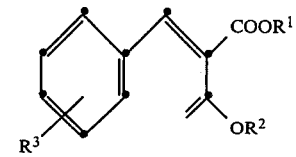

wherein $R^2$ is $(C_1-C_{12})$alkyl or $(C_2-C_{12})$ acyl and heating said compound at a temperature effective to cyclize said compound and form said 2-naphthanoic acid or ester thereof.

* * * * *